(12) United States Patent
Roundhill

(10) Patent No.: US 10,040,777 B2
(45) Date of Patent: Aug. 7, 2018

(54) POLYMERS, CO-POLYMERS, AND MONOMERS USING CO₂ AS A REAGENT

(71) Applicant: Empire Technology Development LLC, Wilmington, DE (US)

(72) Inventor: David Max Roundhill, Seattle, WA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 664 days.

(21) Appl. No.: 14/316,527

(22) Filed: Jun. 26, 2014

(65) Prior Publication Data

US 2015/0376331 A1 Dec. 31, 2015

(51) Int. Cl.
*C07D 317/38* (2006.01)
*C08G 64/02* (2006.01)
*C08G 64/06* (2006.01)
*C08G 64/32* (2006.01)
*C08G 64/34* (2006.01)

(52) U.S. Cl.
CPC ....... *C07D 317/38* (2013.01); *C08G 64/0208* (2013.01); *C08G 64/06* (2013.01); *C08G 64/32* (2013.01); *C08G 64/326* (2013.01); *C08G 64/34* (2013.01)

(58) Field of Classification Search
CPC ...... C08G 64/00; C08G 64/02; C08G 64/002; C08G 64/0219; C08G 64/1608; C08G 63/00
See application file for complete search history.

(56) References Cited

U.S. PATENT DOCUMENTS

| | | | | |
|---|---|---|---|---|
| 2,843,567 A * | 7/1958 | Williams | ........... | C08G 64/1608 528/370 |
| 3,585,168 A * | 6/1971 | Tsurta et al. | ....... | C08G 64/0208 502/152 |
| 3,699,079 A * | 10/1972 | Haynes | ............... | C08G 64/0208 106/10 |
| 4,761,456 A * | 8/1988 | Lund | ......................... | C08F 8/42 525/250 |
| 6,686,435 B1 * | 2/2004 | Petrovic | ............... | C07D 303/42 524/589 |
| 8,163,867 B2 * | 4/2012 | Lee | ......................... | C08G 64/34 502/167 |
| 8,748,555 B2 * | 6/2014 | Allen | ...................... | B32B 27/36 428/220 |
| 9,006,425 B2 * | 4/2015 | North | ...................... | C07F 5/069 544/64 |
| 2014/0031519 A1* | 1/2014 | Zander | ................. | B01J 31/0202 528/412 |
| 2015/0024931 A1* | 1/2015 | Tour | ......................... | B01J 20/20 502/402 |
| 2015/0274882 A1* | 10/2015 | Kim | ..................... | C08G 59/685 528/406 |

FOREIGN PATENT DOCUMENTS

JP 46-002031 A1 * 10/1971
WO WO 2013034750 A2 * 3/2013 .......... B01J 31/2243

OTHER PUBLICATIONS

Walters. The Many Faces of Carbon Dioxide. Science and Technology Review Oct. 2000, pp. 13-15. retrieve online. Retrieved one [Apr. 1, 2016]. Retrieved from internet <URL:https://str.llnl.gov/str/pdfs/10_00.2.pdf>.*
Inoue, S., Koinuma, H. and Tsuruta, T. (1969), Copolymerization of carbon dioxide and epoxide with organometallic compounds. Makromol. Chem., 130: 210-220.*
Inoue, S., Koinuma, H. and Tsuruta, T. (1969), Copolymerization of carbon dioxide and epoxide. J. Polym. Sci. B Polym. Lett., 7: 287-292.*
"CW UV Lasers," Markettech, accessed at http://web.archive.org/web/20131018114805/http://markettechinc.net/Products/CW_UV_lasers.aspx, accessed on Oct. 18, 2014, p. 1.
Datchi, F. et al., "Structure of Polymeric Carbon Dioxide CO2-V," Phys. Rev. Lett., vol. 108, Mar. 19, 2012, pp. 125701-1-125701-5.
"Density," Wikipedia, accessed at http://web.archive.org/web/20140401024755/http://en.wikipedia.org/wiki/Density, last modified on Mar. 28, 2014, pp. 1-12.
"Gas," Wikipedia, accessed at http://web.archive.org/web/20140321172923/http://en.wikipedia.org/wiki/Gas, last modified on Mar. 13, 2014, pp. 1-19.
"Liquid," Wikipedia, accessed at http://web.archive.org/web/20140319010218/http://en.wikipedia.org/wiki/Liquid, last modified on Mar. 13, 2014, pp. 1-12.
Office of Fossil Energy, "Recycling Carbon Dioxide to Make Plastics," May 20, 2013, accessed at http://energy.gov/fe/articles/recycling-carbon-dioxide-make-plastics, accessed on Jun. 26, 2014, 4 pages.
Patel, P., "Carbon-Dioxide Plastic Gets Funding," MIT Technology Review, Nov. 14, 2007, accessed at http://www.technologyreview.com/news/409047/carbon-dioxide-plastic-gets-funding/, accessed Jun. 26, 2014, 2 pages.
"Plasma (physics)," Wikipedia, accessed at http://web.archive.org/web/20140301075425/http://en.wikipedia.org/wiki/Plasma_(physics), last modified on Feb. 24, 2014, pp. 1-26.
"Prandtl-Meyer expansion fan," Wikipedia, accessed at http://web.archive.org/web/20130707095446/http://en.wikipedia.org/wiki/Expansion_fan, last modified on Apr. 20, 2013, pp. 1-7.
"Pressure," Wikipedia, accessed at http://web.archive.org/web/20140319071500/http://en.wikipedia.org/wiki/Pressure, last modified on Mar. 14, 2014, pp. 1-19.

(Continued)

*Primary Examiner* — Sanza Mcclendon

(57) ABSTRACT

Polymers, co-polymers, and monomers using CO₂ as a reagent and methods of production thereof are described. Polymerization methods include converting CO₂ into a polymerizable monomer by exciting the CO₂ with a light source. Such polymers and co-polymers can comprise two or more consecutive repeating units of Formula I:

(I)

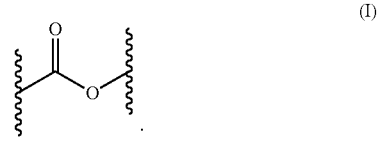

19 Claims, 1 Drawing Sheet

(56) References Cited

OTHER PUBLICATIONS

Sengupta, A. et al., "Polymerization of Carbon Dioxide: A Chemistry View of Molecular-to-Nonmolecular Phase Transitions," Journal of Physical Chemistry C, 2012, vol. 116, pp. 2061-2067.
"Solid," Wikipedia, accessed at http://web.archive.org/web/20131229081539/http://en.wikipedia.org/wiki/Solid, last modified on Dec. 23, 2013, pp. 1-18.
"Temperature," Wikipedia, accessed at http://web.archive.org/web/20140422054536/http://en.wikipedia.org/wiki/Temperature, last modified on Apr. 17, 2014, pp. 1-25.
"Vacuum Ultraviolet Light-Source, 30nm+," McPherson, accessed at http://web.archive.org/web/20120104100137/http://www.mcphersoninc.com/pressreleases/vuv629.htm, accessed on Jun. 18, 2014, pp. 1-1.
"Vacuum UV Light Sources for Laboratory and Production Applications," Heraeus, accessed at http://www.heraeus-noblelight.com/media/webmedia_local/media/pdf/oa/VUV_Brochure2012.pdf, accessed on Jun. 18, 2014, pp. 1-5.
"VUV-UV Grade Opical Windows," eSource Optics, accessed at http://web.archive.org/web/20131004124716/http://www.esourceoptics.com/vuvwindows.html, accessed on Jun. 18, 2014, pp. 1-4.
"Wave," Wikipedia, accessed at http://web.archive.org/web/20140412120033/http://en.wikipedia.org/wiki/Wave, last modified on Apr. 11, 2014, pp. 1-20.
Seely, J. F., et al., "Absolutely calibrated vacuum ultraviolet spectra in the 150-250-nm range from plasmas generated by the NIKE KrF laser," Physics of Plasmas, vol. 12, pp. 062701-1-062701-9 (2005).
Tomasino, D., "Pressure-Induced Phase Transition and Polymerization of Tetracyanoethylene (TCNE)," The Journal of Chemical Physics, vol. 138, No. 9, pp. 094506-1-094506-10 (2013).
Walter, K., "The Many Faces of Carbon Dioxide," accessed at http://web.archive.org/web/20130522194456/https://www.llnl.gov/str/Yoo.html, accessed on Jun. 24, 2014, pp. 1-4.
Whitfield, M., "Innovation Awards: Polymers put CO2 to use," ICIS Chemical Business, Oct. 17, 2011, accessed at http://www.icis.com/Articles/2011/10/17/9500368/innovation-awards-polymers-put-co2-to-use.html, accessed Jun. 26, 2014, 2 pages.
Yan, W-B., et al., "An all-solid-state, deep-UV laser source at 193 nm," Summaries of Papers Presented at the Conference on Lasers and Electro-Optics, p. 485 (1997).

\* cited by examiner

POLYMERS, CO-POLYMERS, AND MONOMERS USING $CO_2$ AS A REAGENT

FIELD

The present technology relates generally to the field of polymeric materials and processes for producing monomers and polymers.

BACKGROUND

The following description is provided to assist the understanding of the reader. None of the information provided or references cited is admitted to be prior art in the present technology.

A form of carbon dioxide ($CO_2$), designated $CO_2$—V, was previously produced under conditions of high pressure and high temperature. However, $CO_2$—V is unstable and collapses at temperatures at or below 21° C. and pressures at or below 1 gigapascal.

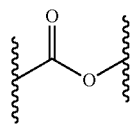

$CO_2$-V

SUMMARY

In one aspect polymeric materials are formed using $CO_2$ as a reagent. The polymers of the present technology include $CO_2$ polymers and $CO_2$ co-polymers that individually comprise one or two or more consecutive repeating units of Formula I:

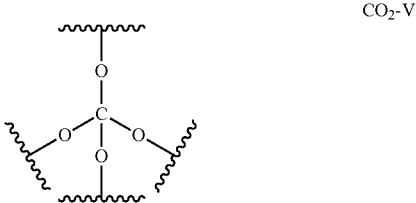

(I)

According to another aspect, the polymer or co-polymer comprises three or more consecutive repeating units of Formula I.

According to one aspect, a composition is provided that includes a polymer of two or more consecutive repeating units of Formula I.

In another aspect, a co-polymer is provided that comprises one or two or more consecutive repeating units of Formula I and a second polymerized monomer.

According to another aspect, a co-polymer is provided that comprises one or two or more consecutive repeating units of Formula I and one or two or more different second polymerized monomers.

According to another aspect, a composition is provided that includes a co-polymer of one or two or more consecutive repeating units of Formula I.

In another aspect, a method of preparing a polymer is provided. The method includes converting $CO_2$ into a polymerizable monomer by exciting the $CO_2$ with a light source.

In another aspect, a method of preparing a co-polymer is provided. The method includes converting $CO_2$ into a polymerizable monomer by exciting the $CO_2$ with a light source in the presence of a second polymerizable monomer. According to one aspect, the method includes converting $CO_2$ into a polymerizable monomer by exciting the $CO_2$ with a light source in the presence of one or two or more different polymerizable monomers.

In another aspect, a method of preparing a monomer is provided. The method includes converting $CO_2$ to an excited reactive state with a light source in the presence of one or more of an olefin, heterocycle, cyclopropane, or cyclobutane.

The foregoing summary is illustrative only and is not intended to be in any way limiting. In addition to the illustrative aspects, embodiments and features described above, further aspects, embodiments and features will become apparent by reference to the following drawings and the detailed description.

DETAILED DESCRIPTION

Figure 1:
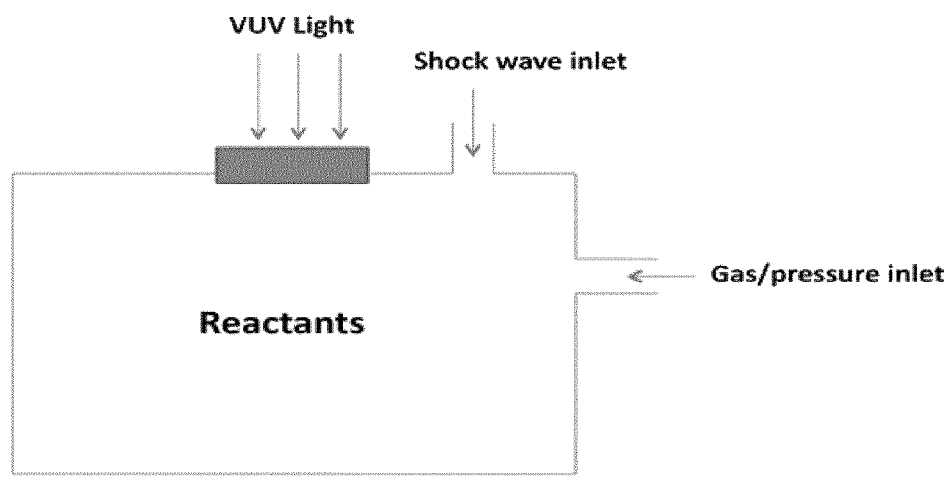
FIG. 1 is a schematic of a gas phase reactor vessel according to one embodiment for the method of producing a polymer, co-polymer, or monomer.

The present technology is described herein using several definitions, as set forth throughout the specification.

As used herein, unless otherwise stated, the singular forms "a," "an," and "the" include plural reference.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, "polymerization" refers to a chemical process in which molecules of carbon-containing compounds are covalently linked to form a polymer with repeating structural units derived from such compounds. Carbon-containing compounds which can undergo polymerization to provide the repeating structural units of a polymer are termed "polymerizable monomers."

As used herein, a "polymer" is an organic compound that includes repeating structural units derived from polymerizable monomers that have been covalently linked together, that is, the polymerizable monomers have undergone polymerization. In some embodiments, the polymer includes at least 3, at least 4, at least 5, or at least 10 repeating structural units. The polymerized monomers making up the polymer may all have the same structure (homopolymer) or may be different (copolymer). A co-polymer includes polymerized monomers of two or more structurally different polymerized monomers. A co-polymer includes random, alternating, and block co-polymers. A random co-polymer includes two or more different polymerized monomers linked in a random order. An alternating co-polymer includes two or more different polymerized monomers that regularly alternate. For example, a co-polymer with polymerized monomers of A and B form an alternating co-polymer such as (-A-B-A-B-A-B-)$_n$. A block co-polymer includes two or more different homopolymers that are covalently linked. For example, a co-polymer with polymerized monomers of A and B may form a block co-polymer such as $(-A-A-A-)_n(-B-B-B-)_m$.

As described herein, an inert gas is a gas that chemically reacts with few or no substances. Inert gases include gases such as nitrogen gas ($N_2$) and noble gases such as argon (Ar).

In general, "substituted" refers to a group, in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. In some embodiments, a substituted group is substituted with 1, 2, 3, 4, 5, or 6 substituents. Examples of substituent groups include: halogens (for example, F, Cl, Br, and I), hydroxyl (alcohol), alkoxy, alkenoxy, alkynoxy, aryloxy, aralkyloxy, carbonyls (oxo), carboxyls, esters, ketones, amides, urethanes, thiols, sulfides, sulfoxides, sulfones, sulfonyls, sulfonamides, amines, isocyanates, isothiocyanates, cyanates, thiocyanates, nitro groups, nitriles (for example, CN), phosphoryl, phosphonyl, aryl, olefin, alkyl, cycloalkyl and the like.

Alkyl groups include straight chain and branched alkyl groups having from 1 to 20 carbon atoms or, in some embodiments, from 1 to 12, 1 to 8, 1 to 6, or 1 to 4 carbon atoms. Alkyl groups further include cycloalkyl groups. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above.

"Cycloalkyl" groups as used herein refers to non-aromatic ring compounds containing 3-10 carbon members. Substituted cycloalkyl groups include cycloalkyl groups substituted one or more times with substituents as those listed above. "Cyclopropane" as used herein refers to non-aromatic ring compounds containing 3 carbon members. "Cyclobutane" as used herein refers to non-aromatic ring compounds containing 4 carbon members. Examples of substituted cycloalkyl groups include, but are not limited to, halocyclopropane, hydroxycyclopropane, alkoxycyclobutane, and cyclobutamine.

"Olefin" as used herein refers to straight and branched chain alkene or cyclic alkene compounds containing 2-14 carbons and at least one double bond between two carbon atoms. In some embodiments the alkenyl group includes 2-8, 2-6, 2-5, or 3-4 carbons. Examples include, but are not limited to vinyl, allyl, $CH=CH(CH_3)$, $CH=C(CH_3)_2$, $C(CH_3)=CH_2$, $C(CH_3)=CH(CH_3)$, $C(CH_2CH_3)=CH_2$, butadienyl, pentadienyl, and hexadienyl, among others. Representative substituted alkenyl groups may be mono-substituted or substituted more than once, such as, but not limited to, mono-, di- or tri-substituted with substituents as those listed above including alkyl, oxo, hydroxy, alkyoxy, or halo groups. Olefin groups include cycloolefin groups. Cycloolefin groups include cycloalkyl groups as defined above, having at least one double bond between two carbon atoms. In some embodiments the cycloolefin group may have one, two or three double bonds but does not include aromatic compounds. Cycloolefin groups have from 4 to 14 carbon atoms, or, in some embodiments, 5 to 14 carbon atoms, 5 to 10 carbon atoms, or even 5, 6, 7, or 8 carbon atoms. Examples of cycloolefin groups include cyclohexenyl, cyclopentenyl, cyclohexadienyl, cyclobutadienyl, and cyclopentadienyl.

"Heterocycle" as used herein refers to non-aromatic ring compounds containing 3 to 7 or possibly higher ring members, of which one or more is a heteroatom such as, but not limited to, N, O, P and S. Heterocycles include cyclic ethers, cyclic amines, lactones, lactams, cyclic anhydrides, and cyclic imides. In some embodiments, heterocyclic groups include 3 to 6, 3 to 5, or 3 to 4 ring members. Heterocyclic groups encompass partially unsaturated and saturated ring systems, such as, for example, imidazolinyl and imidazolidinyl groups. Heterocyclic groups include fused rings and may include an aromatic group fused to a non-aromatic group, for example, dihydrobenzofuran. The phrase also includes bridged polycyclic ring systems containing a heteroatom such as, but not limited to, quinuclidinyl. However, the phrase does not include heterocyclic groups that have other groups, such as alkyl or halo groups, bonded to one of the ring members. Rather, these are referred to as "substituted heterocyclic groups". Heterocyclic groups include, but are not limited to, aziridinyl, azetidinyl, pyrrolidinyl, imidazolidinyl, pyrazolidinyl, thiazolidinyl, tetrahydrothiophenyl, oxiranyl, oxetanyl, tetrahydrofuranyl, dioxolyl, piperidinyl, piperazinyl, morpholinyl, thiomorpholinyl, tetrahydropyranyl, tetrahydrothiopyranyl, quinuclidinyl groups. Representative substituted heterocyclic groups may be mono-substituted or substituted more than once, such as, but not limited to, pyrrolioodinyl or oxazolidinyl groups, which are 2-, 3-, 4-, or 5-substituted, or disubstituted with various substituents such as those listed above. Nitrogen-containing heterocycles are heterocyclic groups that include at least one ring member which is a nitrogen atom. Nitrogen-containing heterocycles include without limitation aziridines, azetidines, pyrrolidine, and piperidine. Substituted nitrogen-containing heterocycles include without limitation butyrolactam and succinimide. Oxygen-containing heterocycles are heterocyclic groups that include at least one ring member which is an oxygen atom. Oxygen-containing heterocycles include without limitation epoxides, oxetanes, tetrahydrofuran, and tetrahydro-2H-pyrans. Substituted oxygen-containing heterocycles include without limitation butyrolactone and succinic anhydride.

"Aryl" as used herein refers to cyclic aromatic hydrocarbons that do not contain heteroatoms. Aryl groups herein include monocyclic, bicyclic and tricyclic ring systems. Thus, aryl groups include, but are not limited to, phenyl, naphthyl, anthracyl, biphenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl, naphthyl, anthracyl, or biphenyl. Although the phrase "aryl groups" includes groups containing fused rings, such as fused aromatic-aliphatic ring systems (for example, indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once with substituents as those listed above. For example, monosubstituted aryl groups include, but are not limited to, 2-, 3-, 4-, 5-, or 6-substituted phenyl or naphthyl groups, which may be substituted with substituents such as those listed above. In some embodiments, the substituted aryl groups fluoro derivatives such as fluorophenyl.

The present technology provides a polymer that comprises two or more consecutive repeating units of Formula I:

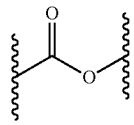

According to one aspect, the polymer comprises three or more consecutive repeating units of Formula I.

In another aspect, a composition is provided that includes a polymer of two or more consecutive repeating units of Formula I.

In another aspect, a co-polymer is provided that comprises one or two or more consecutive repeating units of Formula I and a second polymerized monomer. According to one aspect, the co-polymer is a block co-polymer. In another embodiment, a composition is provided that includes the co-polymer.

According to one aspect, the second polymerized monomer is derived from a polymerizable monomer selected from one or more substituted diol or unsubstituted diol such as, for example, aryl diols, biphenyl diols, alkyl diols, and cycloalkyl diols. The substituted diol or unsubstituted diol also includes naphthalene diols and anthracene diols. In some embodiments the substituted diol or unsubstituted diol is selected from one or more of 4,4'-(propane-2,2-diyl) diphenol (bisphenol A); 1,4-hydroquinone; 4,4'-dihydroxybiphenyl; 1,5-dihydroxynaphthalene; 9,10-dihydroxyanthracene; 4,4'-(methane-2,2-diyl)diphenol; 4,4'-(ethane-2,2-diyl)diphenol; or isomers thereof.

In another aspect, a method of preparing a polymer is provided. The method includes converting $CO_2$ into a polymerizable monomer by exciting the $CO_2$ with a light source. As will be understood by those of skill in the art, $CO_2$ may converted to a polymerizable monomer when it is sufficiently excited by light. As will be understood from the description below, typical incandescent, fluorescent and LED light fixtures are not generally suitable light sources as they typically do not convert $CO_2$ into a sufficiently excited state to undergo polymerization.

In another aspect, a method of preparing a co-polymer is provided. According to one aspect, the co-polymer is a block co-polymer. In another aspect, the co-polymer is a random co-polymer. In another aspect, the co-polymer is an alternating co-polymer. The method includes converting $CO_2$ into a polymerizable monomer by exciting the $CO_2$ with a light source in the presence of a second polymerizable monomer. According to one aspect, the method includes converting $CO_2$ into a polymerizable monomer by exciting the $CO_2$ with a light source in the presence of one or two or more different second polymerizable monomers.

In another embodiment, a method of preparing a first polymerizable monomer is provided. The process includes converting $CO_2$ to an excited reactive state with a light source in the presence of one or more substituted olefin, unsubstituted olefin, heterocycle, cyclopropane, or cyclobutane. The first polymerizable monomer may be polymerized with like monomers or with different monomers (for example, a second polymerizable monomer) to form homopolymers or co-polymers, respectively.

According to one embodiment, the method of preparing a polymer, co-polymer, or monomer can be performed in a reactor at generally any temperature, such as a temperature of about −50° C. to about 350° C. In another embodiment the temperature may be about 0° C. to about 250° C. In another embodiment the temperature may be about 50° C. to about 150° C. In another embodiment the temperature may be about 50° C., about 100° C., about 150° C., about 200° C., about 250° C., about 300° C., about 350° C., or ranges between any two of these values (including endpoints). The pressure in the reactor may generally be any pressure, such as about 100 KPa to about 10,000 KPa. The pressure in the reactor may be about 200 KPa to about 5,000 KPa. The pressure in the reactor may be about 300 KPa to about 3,000 KPa. In another embodiment the pressure may be about 9000 KPa, about 8000 KPa, about 7000 KPa, or about 6000 KPa. Specific examples of pressures include about 100 KPa, about 200 KPa, about 300 KPa, about 400 KPa, about 500 KPa, about 1000 KPa, about 2000 KPa, about 3000 KPa, about 4000 KPa, about 5000 KPa, about 6000 KPa, about 7000 KPa, about 8000 KPa, about 9000 KPa, about 10000 KPa, or ranges between any two of these values (including endpoints). In one embodiment, the pressure will be static pressure. In another embodiment, the pressure will be induced by a pulsed shock wave. The method may be performed in the presence of at least one light source. In one embodiment, the pulsed shock wave may be generated by one or more piezoelectronic or electromagnetic shock wave generators, one or more femtosecond or other pulse lasers, by a detonation method, or another methods known to those skilled in the art. In one embodiment, $CO_2$ is present in the reactor. In another embodiment, $CO_2$ and an inert gas, or $CO_2$ and inert gas mixture are present in the reactor. In another embodiment, $CO_2$ and one or more second polymerizable monomers are present in the reactor. In another embodiment, $CO_2$, one or more second polymerizable monomers, and an inert gas or inert gas mixture are present in the reactor. In another embodiment, $CO_2$ and a substituted olefin, unsubstituted olefin, heterocycle, cyclopropane, or cyclobutane are present in the reactor. In another embodiment, $CO_2$, a substituted olefin, unsubstituted olefin, heterocycle, cyclopropane, or cyclobutane are present in the reactor and an inert gas or inert gas mixture are present in the reactor. In one embodiment at least one radical initiator is added to the reactor. A variety of radical initiators may be used in accordance with the present technology. In one embodiment, the radical initiator includes one or more of a persulfate, an azo compound, or an azoisoalkylnitrile.

According to one embodiment, $CO_2$, the second polymerizable monomer, and/or substituted or unsubstituted olefin, heterocycle, cyclopropane, or cyclobutane are gases. In another embodiment, the $CO_2$, the second polymerizable monomer, and/or substituted or unsubstituted olefin, heterocycle, cyclopropane, or cyclobutane are liquids. In another embodiment, the $CO_2$ is a supercritical fluid.

According to one embodiment, the method may be carried out in the presence of at least one terminating agent. A variety of terminating agents may be used in accordance with the present technology including an alcohol. In another embodiment, the terminating agent is a secondary alcohol. In another embodiment, the alcohol is selected from one or more of 2-propanol; 2-butanol; 2-pentanol; 2-hexanol; 3-hexanol; 1,3-butanediol; 2,3-butanediol; 3-methyl-2-butanol; cyclohexanol; cyclopentanol; 4-hydroxyphenylmethylcarbinol; 3-methyl-4-hydroxyphenylmethylcarbinol; 4-acetoxyphenylmethylcarbinol; 1,2-propanediol; 3-hydroxytetrahydrofuran; 4-hydroxy-2-oxopentanoic acid; 3,3-dimethyl-2-butanol; endo-1,7,7-trimethyl-bicyclo[2.2.1]heptan-2-ol.

In another embodiment, the polymerization terminates to form a cyclic polymer or cyclic co-polymer. In another embodiment, a cyclic monomer is formed.

It will be understood by those of skill in the art that a light source of the present technology is sufficiently high energy (that is, short wavelength and high frequency) to convert carbon dioxide into an excited state that allows for polymerization of the carbon dioxide. Hence, sunlight and typical room lights (for example, incandescent, fluorescent, LED) typically cannot act as light sources for the present technology as they are not $CO_2$-polymerizing light sources.

According to one embodiment of the present technology, the light source is a laser. In some embodiments, the light source is an ultra-violet (UV) laser. In another aspect, the light source is a lamp. In some embodiments, the light source is an ultra-violet (UV) lamp. In some embodiments, the light source is a vacuum ultra-violet (VUV) light source. In one embodiment the VUV light source has a wavelength of about 10 nm to about 200 nm or about 5 nm to about 400 nm. In another embodiment the VUV light source has a wavelength of about 10 nm to about 115 nm. In another embodiment the VUV light source has a wavelength of about 5 nm, about 10 nm, 20 nm, about 30 nm, about 40 nm, about 50 nm, about 60 nm, about 70 nm, about 80 nm, about 90 nm, about 100 nm, about 200 nm, about 300 nm, about 400 nm, or ranges between any two of these values (including endpoints). In one embodiment the VUV light source has a frequency of about 750 THz to about 60,000 THz. In one embodiment the VUV light source has a frequency of about 2600 THz to about 30,000 THz. In another embodiment the VUV light source has a frequency of about 3330 THz, about 7500 THz, about 15,000 THz, or about 30,000 THz. Specific examples of frequencies include about 750 THz, about 1,000 THz, about 5,000 THz, about 10,000 THz, about 20,000 THz, about 30,000 THz, about 40,000 THz, about 50,000 THz, about 60,000 THz, and ranges between any two of these values (including endpoints). In one embodiment, the VUV light source may include at least one deuterium lamp. The deuterium lamp can generally have any power, such as a power range of about 10 watts to about 400 watts. In another embodiments, the VUV light source may include at least one deuterium lamp including a power range of about 200 to about 400 watts. In another embodiment, the VUV light source may include at least one deuterium lamp including a power range of about 30 watts, about 50 watts, about 100 watts, about 200 watts, or about 400 watts. Specific examples of power include about 10 watts, about 20 watts, about 30 watts, about 40 watts, about 50 watts, about 100 watts, about 200 watts, about 300 watts, about 400 watts, or ranges between any two of these values (including endpoints). In one embodiment, the VUV light source is connected to at least one optical window made of an appropriate material. In one embodiment, the optical window material includes a VUV grade magnesium fluoride window, calcium fluoride window, and/or synthetic silica window. In one embodiment, the optical window is about 2 mm to about 10 mm thick. In another embodiment, the optical window is about 2 mm to about 8 mm, 3 mm to about 7 mm, or about 5 mm to about 7 mm thick. Specific examples of thicknesses include about 2 nm, about 3 nm, about 4 nm, about 5 nm, about 6 nm, about 7 nm, about 8 nm, about 9 nm, about 10 nm, and ranges between any two of these values (including endpoints).

According to one embodiment, the method of converting $CO_2$ into a polymerizable monomer; the method of converting $CO_2$ into a polymerizable monomer in the presence of one or more polymerizable second monomers; and/or the method of preparing a monomer including converting $CO_2$ to an excited reactive state in the presence of one or more of a substituted olefin, unsubstituted olefin, heterocycle, cyclopropane, or cyclobutane includes periodically subjecting the $CO_2$, $CO_2$ and polymerizable second monomer(s), or $CO_2$ and a substituted olefin, unsubstituted olefin, heterocycle, cyclopropane, or cyclobutane to pressure by a pulsed shock wave. In one embodiment, the pulsed shock wave may be periodically induced. Periodically induced may include inducing the shock wave about 1 to about 100 times per second. In another embodiment, the pulsed shock wave may be induced about 5 to about 50 times per second. In another embodiment, periodically inducing the shock wave may be about 10, about 25, about 50, about 100 times per second, or ranges between any two of these values (including endpoints). In one embodiment, the pulsed shock wave causes a pressure increase of about 100 to about 300 KPa. In another embodiment, the pulsed shock wave causes a pressure increase of about 125 to about 200 KPa. In another embodiment, the pulsed shock wave causes a pressure increase of about 100, about 125, about 150, about 175, about 200, about 250, about 300 KPa, or ranges between any two of these values (including endpoints).

EXAMPLES

The following examples more specifically illustrate protocols for preparing polymers according to various embodiments described above. These examples should in no way be construed as limiting the scope of the present technology.

Example 1: Preparation of a $CO_2$ Polymer

A polymer is produced as follows. $CO_2$ is introduced into a reactor vessel through a gas/pressure inlet tube attached to the reactor vessel chamber. The temperature of the reactor vessel is adjusted to about −50° C. to about 0° C. The pressure in the reactor vessel chamber is controlled with external valves and gauges connected to the gas inlet tube and $CO_2$ source and is about 100 KPa to about 10,000 KPa. The reactor vessel is equipped with a VUV grade magnesium fluoride transport window with an attached VUV laser with a deuterium lamp having a wavelength of about 115 nm to about 400 nm and frequency of about 750 THz to about 2600 THz. Another inlet tube is attached to the reactor vessel chamber that is in turn connected to a pulsed shock wave system, and a pulsed shock wave from about 1 to about 5 times per second is introduced into the reactor vessel chamber, causing a pressure increase of about 100 KPa to about 125 KPa. A $CO_2$ polymer is produced in the reactor vessel chamber. Following production of the $CO_2$ polymer, the polymer is collected from the reactor vessel chamber.

Example 2: Preparation of a $CO_2$ and 4,4'-(ethane-2,2-diyl)diphenol co-polymer A co-polymer is produced by introducing $CO_2$ into a reactor vessel through a gas/pressure inlet tube attached to the reactor vessel chamber. Through a second gas/pressure inlet tube 4,4'-(ethane-2,2-diyl)diphenol is introduced into the reactor vessel chamber. The temperature of the reactor vessel is adjusted to about 0° C. to about 250° C. The pressure in the reactor vessel chamber is controlled with external valves and gauges connected to the gas inlet tube and $CO_2$ source to be from about 200 KPa to about 5,000 KPa. The reactor vessel is equipped with a VUV grade calcium fluoride transport window with an attached VUV laser with an attached VUV laser with a deuterium lamp having a wavelength of about 40 nm to about 90 nm and frequency of about 3330 THz to about 7500 THz. Another inlet tube is attached to the reactor vessel chamber that is in turn connected to a pulsed shock wave system, and a pulsed shock wave of about 5 to about 50 times per second is introduced into the reactor vessel chamber, causing a pressure increase of about 200 to about 300 KPa. The co-polymer is produced in the reactor vessel chamber. Following production of the co-polymer, the co-polymer is collected from the reactor vessel chamber.

Example 3: Preparation of an Ethylene Carbonate Monomer and Polycarbonate Co-Op A monomer is produced by introducing $CO_2$ and ethylene oxide into a reactor vessel through a gas inlet tube attached to the reactor vessel chamber. The temperature of the reactor vessel is maintained at about 150° C. to about 250° C. The pressure in the reactor vessel chamber is adjusted to about 300 KPa to about 3,000 KPa. The reactor vessel is equipped with a VUV grade magnesium fluoride transport window with an attached VUV laser with a deuterium lamp having a wavelength of about 5 nm to about 90 nm. Another inlet tube is attached to the reactor vessel chamber that is in turn connected to a pulsed shock wave system, a pulsed shock wave of about 50 to about 150 times per second is introduced into the reactor vessel chamber, causing a pressure increase of about 250 to about 300 KPa. The ethylene carbonate monomer product is collected from the reactor vessel chamber and can be polymerized with bisphenol A under known reaction conditions to produce a polycarbonate polymer.

Example 4: Preparation of a Gas Phase Reactor Vessel

A gas phase reactor vessel for carrying out the method is shown in FIG. 1. The reactor housing may be fabricated from chemically resistant materials such as chemically resistant steel. The VUV window may be a transparent window sealed into a hole made of an appropriate material for transporting VUV light. One or more gas/pressure inlets may be sealed into holes on the side or top of the reactor vessel. The gas/pressure inlet(s) may be attached to external valves and/or gauges that are in turn connected to a vacuum. The gas/pressure inlet(s) may be attached to external valves and/or gauges that are in turn connected to a source of $CO_2$; second polymerizable monomer(s); substituted or unsubstituted olefin, heterocycle, cyclopropane, or cyclobutane; and/or inert gas. Optionally, another inlet may be connected to the reactor vessel, which is in turn connected to a pulsed shock wave system. The polymer or monomer product(s) may be recovered from the reactor vessel at the end of the process.

Figure 2:
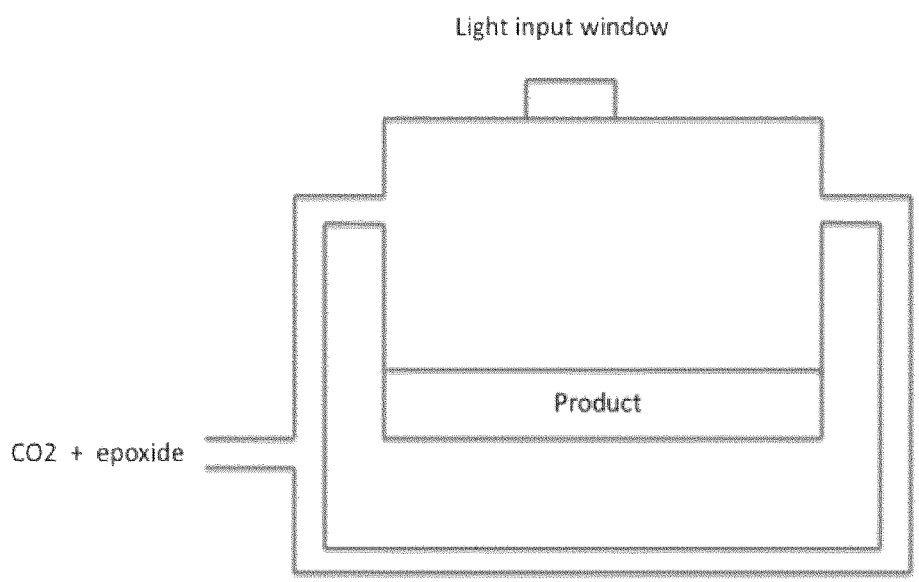
FIG. 2 is a schematic of a gas phase reactor vessel according to another embodiment for the method of producing a polymer, co-polymer, or monomer.

An alternative gas phase reactor vessel that may be used for carrying out the method is shown in FIG. 2. The reactor housing may be fabricated from chemically resistant materials such as chemically resistant steel. The light input window or VUV window may be a transparent window sealed into a hole made of an appropriate material for transporting VUV light. A gas/pressure inlet and outlet may be sealed into holes on the sides or top of the reactor vessel to allow a continuous flow of $CO_2$; second polymerizable monomer(s); substituted or unsubstituted olefin, heterocycle, cyclopropane, or cyclobutane; and/or inert gas. The gas/pressure may be controlled as it flows into the inlet tube that leads to the reactor vessel. Optionally, another inlet may be connected to the reactor vessel, which is in turn connected to a pulsed shock wave system. The polymer or monomer product(s) may be recovered from the reactor vessel at the end of the process.

The gas reactor vessel optionally may have an outlet valve connected to the bottom of the reaction chamber to allow the product to be removed on a continuous basis. Preferably a reactor vessel with an outlet valve sealed to the bottom of the reaction chamber is used for liquid products.

The illustrative embodiments described in the detailed description and claims are not meant to be limiting. Other embodiments may be used, and other changes may be made, without departing from the spirit or scope of the subject matter presented here.

EQUIVALENTS

The embodiments, illustratively described herein may suitably be practiced in the absence of any element or elements, limitation or limitations, not specifically disclosed herein. Thus, for example, the terms 'comprising,' 'including,' 'containing,' etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Similarly, the phrase "at least about" some value such as, for example, wt % includes at least the value and about the value. For example "at least about 1 wt %" means "at least 1 wt % or about 1 wt %." Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed is:

1. A co-polymer comprising two or more consecutive repeating units of Formula I:

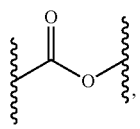

(I)

and a second polymerized monomer derived from a second polymerizable monomer selected from one or more of substituted diol or unsubstituted diol;
wherein the co-polymer is a block co-polymer, random co-polymer, or alternating co-polymer.

2. The co-polymer of claim 1, wherein the second polymerizable monomer is one or more of 4,4'-(propane-2,2-diyl)diphenol; 1,4-hydroquinone; 4,4'-dihydroxybiphenyl; 1,5-dihydroxynaphthalene; 9,10-dihydroxyanthracene; 4,4'-(methane-2,2-diyl)diphenol; 4,4'-(ethane-2,2-diyl)diphenol; and isomers thereof.

3. A method of preparing a polymer or a co-polymer comprising two or more consecutive repeating units of Formula I:

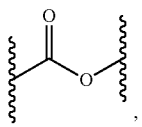

(I)

the method comprising converting carbon dioxide into a polymerizable monomer by exciting the carbon dioxide with a light source;
wherein the light source has a wavelength of about 5 nm to about 400 nm.

4. The method of claim 3, wherein the carbon dioxide is excited in the presence of a second polymerizable monomer.

5. The method of claim 3, wherein the carbon dioxide is excited in the presence of a terminating agent.

6. The method of claim 5, wherein the terminating agent is one or more of 2-propanol; 2-butanol; 2-pentanol; 2-hexanol; 3-hexanol; 1,3-butanediol; 2,3-butanediol; 3-methyl-2-butanol; cyclohexanol; cyclopentanol; 4-hydroxyphenylmethylcarbinol; 3-methyl-4-hydroxyphenylmethylcarbinol; 4-acetoxyphenylmethylcarbinol; 1,2-propanediol; 3-hydroxytetrahydrofuran; 4-hydroxy-2-oxopentanoic acid; 3,3-dimethyl-2-butanol; and endo-1,7,7-trimethyl-bicyclo[2.2.1]heptan-2-ol.

7. The method of claim 3, wherein the polymer or co-polymer is a cyclic polymer or cyclic co-polymer.

8. The method of claim 4, wherein the second polymerizable monomer is one or more of a substituted alkyl diol, unsubstituted alkyl diol, cycloalkyl diol, aromatic diol, and biphenyl diol.

9. The method of claim 4, wherein the second polymerizable monomer is one or more of 4,4'-(propane-2,2-diyl)diphenol; 1,4-hydroquinone; 4,4'-dihydroxybiphenyl; 1,5-dihydroxynaphthalene; 9,10-dihydroxyanthracene; 4,4'-(methane-2,2-diyl)diphenol; 4,4'(ethane-2,2-diyl)diphenol; and isomers thereof.

10. The method of claim 3, wherein the light source is a laser, an ultra-violet laser, or a vacuum ultra-violet laser.

11. The method claim 3, wherein the carbon dioxide is a liquid.

12. The method of claim 3, wherein the converting step is performed at a pressure of about 100 KPa to about 10,000 KPa.

13. A method of preparing a first polymerizable monomer, the method comprising converting carbon dioxide to an excited reactive state with a light source in the presence of one or more substituted olefin, unsubstituted olefin, heterocycle, cyclopropane, or cyclobutane;
wherein the light source has a wavelength of about 5 nm to about 400 nm.

14. The method of claim 13, wherein the heterocycle is one or more of a substituted cyclic ether, unsubstituted cyclic ether, cyclic amine, lactone, lactam, cyclic anhydride, and cyclic imide.

15. The method of claim 13, wherein the heterocycle is one or more of a substituted epoxide, unsubstituted epoxide, aziridine, oxetane, azetidine, tetrahydrofuran, pyrrolidine, butyrolactone, butyrolactam, succinic anhydride, and succinimide.

16. The method of claim 13, wherein the light source is a laser, an ultra-violet laser, or a vacuum ultra-violet laser.

17. The method of claim 13, wherein the carbon dioxide is a liquid.

18. The method of claim 13, wherein the converting step is performed at a pressure of about 100 KPa to about 10,000 KPa.

19. A composition comprising the co-polymer of claim 1.

* * * * *